US005965782A

United States Patent [19]

Drake et al.

[11] Patent Number: 5,965,782

[45] Date of Patent: Oct. 12, 1999

[54] ZEOLITE CATALYST COMPOSITION AND PROCESSES THEREFOR AND THEREWITH

[76] Inventors: Charles A. Drake, Rte. 1, Box 206, Nowata, Okla. 74048; An-hsiang Wu, 854 Concord Dr., Bartlesville, Okla. 74006

[21] Appl. No.: 09/034,064

[22] Filed: Mar. 3, 1998

Related U.S. Application Data

[62] Division of application No. 08/826,619, Apr. 4, 1997, Pat. No. 5,776,852.

[51] Int. Cl.[6] .............................. C07C 5/22; C07C 4/12; C10G 35/06

[52] U.S. Cl. .......................... 585/475; 585/489; 208/136

[58] Field of Search .................................... 585/475, 489; 208/136

[56] References Cited

U.S. PATENT DOCUMENTS

| | | | |
|---|---|---|---|
| 4,501,926 | 2/1985 | LaPierre et al. | 585/739 |
| 4,518,485 | 5/1985 | LaPierre | 208/89 |
| 5,321,161 | 6/1994 | Vreugdenhil et al. | 564/490 |
| 5,338,716 | 8/1994 | Triplett et al. | 502/64 |
| 5,776,852 | 7/1998 | Wu et al. | 502/177 |

*Primary Examiner*—Walter D. Griffin
*Assistant Examiner*—Thuan D. Dang
*Attorney, Agent, or Firm*—Richmond, Hitchcock, Fish & Dollar

[57] ABSTRACT

A catalyst composition, a process for producing the composition and a process for transalkylation of $C_9$+ aromatic compounds to $C_6$ to $C_8$ aromatic hydrocarbons are disclosed. The composition comprises a zeolite and tungsten wherein tungsten is preferably present as tungsten carbide which is impregnated on the zeolite. A preferred process for producing the catalyst composition which comprises: (1) contacting a zeolite with an effective amount of an acid under a condition sufficient to produce an acid-leached zeolite; and (2) impregnating acid-leached zeolite with an effective amount of tungsten-containing compound under a condition sufficient to effect the production of a tungsten carbide-promoted zeolite. The transalkylation process comprises contacting, in the presence of the catalyst composition, a fluid which comprises a $C_9$+ aromatic compound with a hydrogen-containing fluid under a condition sufficient to effect the conversion of a $C_9$+ aromatic compound to a $C_6$ to $C_8$ aromatic hydrocarbon.

10 Claims, No Drawings

ZEOLITE CATALYST COMPOSITION AND PROCESSES THEREFOR AND THEREWITH

This application is a Division of application Ser. No. 08/826,619 filed Apr. 4, 1997, now U.S. Pat. No. 5,776,852.

FIELD OF THE INVENTION

This invention relates to a catalyst composition useful for converting $C_9$+ aromatic compounds as well as naphthalene to $C_6$ to $C_8$ aromatic hydrocarbons, to a process for producing the composition, and to a process for using the composition.

BACKGROUND OF THE INVENTION

It is well known to those skilled in the art that aromatic hydrocarbons are a class of very important industrial chemicals which find a variety of uses in petrochemical industry. Recent efforts to convert gasoline to more valuable petrochemical products have therefore focused on the conversion of gasoline to aromatic hydrocarbons by catalytic cracking in the presence of zeolite catalysts. The aromatic hydrocarbons produced by the conversion process include benzene, toluene and xylenes (hereinafter collectively referred to as BTX) or $C_6$ to $C_8$ hydrocarbons, which can be useful feedstocks for producing various organic compounds and polymers. However, heavier, less useful aromatic compounds are also produced during the conversion process. Similarly, naphthalene is a relatively low value hydrocarbon which can be converted to more valuable aromatic hydrocarbons such as BTX. Therefore, a catalyst and a process for converting these heavier and less useful aromatic compounds (mainly trimethyl- and tetramethylbenzenes) as well as other low valued hydrocarbons such as naphthalene to the more valuable BTX hydrocarbons would be a significant contribution to the art and to the economics.

SUMMARY OF THE INVENTION

An object of this invention is to provide a catalyst composition which can be used to convert $C_9$+ aromatic compounds to $C_6$ to $C_8$ aromatic hydrocarbons. Also an object of this invention is to provide a process for producing the catalyst composition. Another object of this invention is to provide a process which can employ the catalyst composition to convert $C_9$+ aromatic compounds to $C_6$ to $C_8$ aromatic hydrocarbons. An advantage of the catalyst composition is that it exhibits high transalkylation activity, satisfactory selectivity to xylenes, and good stability. Other objects and advantages will becomes more apparent as this invention is more fully disclosed hereinbelow.

According to a first embodiment of the present invention, a composition which can be used as a catalyst for converting a $C_9$+ aromatic compound to a $C_6$ to $C_8$ aromatic hydrocarbon is provided. The composition comprises, consists essentially of, or consists of, a zeolite and tungsten wherein the weight ratio of tungsten to zeolite is in the range of from about 0.0001:1 to about 0.5:1.

According to a second embodiment of the present invention, a process which can be used for producing a catalyst composition is provided. The process comprises the steps: (1) optionally contacting a zeolite with an acid in an amount and under a condition effective to produce an acid-leached zeolite; (2) contacting a zeolite, which can have been optionally treated with an acid, with a tungsten-containing compound in an amount and under a condition effective to produce a tungsten-incorporated or -impregnated zeolite; (3) calcining the tungsten-incorporated or -impregnated zeolite.

According to a third embodiment of the present invention, a process which can be used for converting a $C_9$+ aromatic compound to a $C_6$ to $C_8$ aromatic compound is provided which comprises, consists essentially of, or consists of, contacting a fluid which comprises a $C_9$+ aromatic compound with a hydrogen-containing fluid in the presence of a catalyst composition which is the same as the composition disclosed above in the first embodiment, and can be produced by the process disclosed in the second embodiment, of the invention under a condition effective to convert a $C_9$+ aromatic compound to an aromatic hydrocarbon containing 6 to 8 carbon atoms per molecule.

DETAILED DESCRIPTION OF THE INVENTION

The composition of the first embodiment of the present can comprise, consists essentially of, or consists of, a zeolite and tungsten. Preferably tungsten is present in the composition in the form of tungsten carbide. Further preferably, tungsten carbide is impregnated or coated on the zeolite. Most preferably, tungsten carbide is impregnated on an acid-leached zeolite.

According to the present invention the weight ratio of tungsten to zeolite can be in the range of from about 0.0001:1 to about 0.5:1, preferably about 0.0005:1 to about 0.3:1, more preferably about 0.001:1 to about 0.2:1, and most preferably 0.01:1 to 0.1:1.

Alternatively, tungsten carbide can be present in the invention composition in the range of from about 0.01 to about 35, preferably about 0.05 to about 30, more preferably 0.1 to about 25, and most preferably about 1 to about 20 grams per 100 grams of the composition. The composition can also be characterized by having the following physical characteristics: a surface area as determined by the BET method using nitrogen in the range of from about 50 to about 1,000, preferably 50 to 500 $m^2/g$; a pore volume in the range of from about 0.1 to about 2.0, preferably about 0.1 to about 1.5, and most preferably 0.1 to 1.0 ml/g; an average pore diameter in the range of from about 10 to about 500, preferably about 5 to about 300, and most preferably 10 to 200 Å; and a porosity of more than about 20%.

The composition of the present invention can be prepared by any methods known to one skilled in the art for producing a tungsten carbide- or any metal carbide-supported catalysts. One such method is disclosed in U.S. Pat. No. 5,573,991, disclosure of which is incorporated herein by reference. For example, the composition can be prepared by incorporating or impregnating a tungsten-containing compound into a zeolite in the weight ratios disclosed above using any methods known to one skilled in the art. However, it is presently preferred that the composition of the present invention be produced by the process disclosed in the second embodiment of the invention.

According to the second embodiment of the invention, a zeolite can be optionally contacted with one or more suitable binders in a liquid, preferably aqueous medium, to form a zeolite-binder mixture. Any binders known to one skilled in the art for use with a zeolite are suitable for use herein. Examples of suitable binder include, but are not limited to, clays such as for example, kaolinite, halloysite, vermiculite, chlorite, attapulgite, smectite, montmorillonite, illite, saconite, sepiolite, palygorskite, diatomaceous earth, and combinations of any two or more thereof; aluminas such as for example $\alpha$-alumina and $\gamma$-alumina; silicas; aluminasilica; aluminum phosphate; aluminum chlorohydrate; and combinations of any two or more thereof. Because these binders are well known to one skilled in the art, description of which is omitted herein. The weight ratio of a zeolite to a binder can be in a wide range and generally in the range of from about 200:1 to about 0.1:1, preferably 100:1 to 0.01:1.

The zeolite and the binder can be well mixed by any means known to one skilled in the art such as stirring, blending, kneading, or extrusion, following which the zeolite-binder mixture can be dried in air at a temperature in the range of from about 20 to about 200° C., preferably about 25 to about 175° C., and most preferably 25 to 150° C. for about 0.5 to about 50 hours, preferably about 1 to about 30 hours, and most preferably 1 to 20 hours, preferably under atmospheric pressure. Thereafter, the dried, zeolite-binder mixture can be further calcined, if desired, in air at a temperature in the range of from about 300 to 2000° C., preferably about 350 to about 1000° C., and most preferably 450 to 750° C. to prepare a calcined zeolite-binder. If a binder is not desired, a zeolite can also be calcined under similar conditions to remove any contaminants, if present.

Any commercially available zeolites can be employed as a starting material of the process of the second embodiment of the invention. Examples of suitable zeolites include, but are not limited to, those disclosed in Kirk-Othmer Encyclopedia of Chemical Technology, third edition, volume 15 (John Wiley & Sons, New York, 1991) and in W. M. Meier and D. H. Olson, "Atlas of Zeolite Structure Types," 138–139, Butterworth-Heineman, Boston, Mass., (3rd ed. 1992). A beta zeolite or zeolite beta that has a framework topology identified as BEA is preferred because, when impregnated thereon tungsten carbide, it is effective in the conversion of $C_9$+ aromatic compound to a $C_6$–$C_8$ aromatic hydrocarbon.

In the first step of the second embodiment of the invention, a zeolite can be optionally contacted with an acid under a condition sufficient to effect the formation of an acid-leached zeolite.

According to the second embodiment of the present invention, the acid can be organic acids, inorganic acids, or combinations of any two or more thereof. The acid can also be a diluted aqueous acid solution. Examples of suitable acids include, but are not limited to sulfuric acid, hydrochloric acid, nitric acid, phosphoric acid, ammonium sulfate, ammonium chloride, ammonium nitrate, formic acid, acetic acid, trifluoroacetic acid, citric acid, trichloroacetic acid, p-toluenesulfonic acid, methanesulfonic acid, partially neutralized acids, wherein one or more protons have been replaced with, for example, a metal (preferably an alkali metal), and combinations of any two or more thereof. Examples of partially neutralized acids include, but are not limited to, sodium bisulfate, sodium dihydrogen phosphate, potassium hydrogen tartarate, and combinations thereof. The presently preferred acid is hydrochloric acid for it is readily available.

Any methods known to one skilled in the art for treating a solid catalyst with an acid can be used in the acid treatment of the present invention. Generally, a zeolite can be suspended in an acid solution. The concentration of the zeolite in the acid solution can be in the range of from about 0.1 to about 800, preferably about 5 to about 700, more preferably about 10 to about 600, and most preferably 15 to 500 grams per liter of acid solution. The amount of acid required is the amount that can maintain the solution in acidic pH during the treatment. Preferably the initial pH of the acid solution containing a zeolite is adjusted to lower than about 3, preferably lower than about 2, more preferably lower than about 1, and most preferably lower than 0.5. Upon the pH adjustment of the solution, the solution can be subjected to a treatment at a temperature in the range of from about 30° C. to about 200° C., preferably about 40° C. to about 150° C., and most preferably 50° C. to 150° C. for about 1 minute to about 30 hours, preferably about 5 minutes to about 20 hours, and most preferably 10 minutes to 10 hours. The treatment can be carried out under a pressure that can maintain or accommodate the temperatures disclosed above and can be in the range of from about 1 to about 10 atmospheres (atm), preferably about 1 atm. Thereafter, the acid-treated zeolite can be washed with a running water for 1 to about 60 minutes followed by drying to produce an acid-leached zeolite. Any drying method known to one skilled in the art such as, for example, air drying, heat drying, spray drying, fluidized bed drying, or combinations of two or more thereof can be used.

The acid-leached zeolite can then be calcined under a sufficient condition similar to that disclosed above for about 1 to about 20, preferably about 2 to about 15, and most preferably 3 to 10 hours.

A zeolite, preferably having been acid treated as disclosed above, can then be treated with a tungsten-containing compound under a condition sufficient to incorporate, preferably impregnate, the tungsten-containing compound into the zeolite. Preferably the condition is sufficient to effect the formation of tungsten carbide which is incorporated into, or impregnated onto, the zeolite.

According to the invention, any tungsten-containing compound which can be incorporated into a zeolite can be used. Examples of suitable tungsten-containing compounds include, but are not limited to, tungsten hexachloride, tungsten tetrachloride, tungsten pentachloride, tungsten, hexabromide, tungsten tetrabromide, tungsten pentabromide, tungsten, hexafluoride, tungsten tetrafluoride, tungsten pentafluoride, tungsten hexacarbonyl, tungsten oxychloride, tungsten, hexasulfide, tungsten tetrasulfide, tungsten pentasulfide, ammonium metatungstate, sodium metatungstate, potassium metatungstate, tungstic acid, and combinations of two or more thereof. A suitable tungsten-containing compound can be incorporated into or impregnated onto a zeolite by any methods known to one skilled in the art such as, for example, incipient wetness method followed by suitable calcination or steam treatment.

Preferably, the incorporation or impregnation of a tungsten-containing compound is carried out under a condition sufficient to effect the production of tungsten carbide. A zeolite can be contacted with a tungsten-containing compound and a carbon-nitrogen compound, in a suitable solvent, at an elevated temperature to produce a tungsten carbide-incorporated or -promoted zeolite. Examples of suitable carbon-nitrogen compounds include, but are not limited to, guanidine, urea, cyanamide, dicyanamide, carbon nitrile, dicyandiamide, cyanoguanidine, or combinations of two or more thereof. The presently preferred carbon-nitrogen compound is guanidine for it is effective in forming tungsten carbide. Examples of suitable solvent include, but are not limited to, ethanol, methanol, propanol, acetone, methyl ethyl ketone, amides, ethers, esters, other alcohols and ketones, or combinations of two or more thereof.

The contacting of zeolite with a tungsten-containing compound and a carbon-nitrogen compound can be carried out under any suitable condition known to one skilled in the art such as, for example, a temperature in the range of from about 10 to about 100° C. under atmospheric pressure for a period to incorporate or impregnate a desired amount of the tungsten-containing compound onto the zeolite. Upon completion of the contacting, a mixture is formed. If there is any excess solvent remaining, it can be removed by any methods known to one skilled in the art. Thereafter, the mixture is subject to calcination. According to the present invention, the calcining step is preferably carried out in the presence of an inert fluid such as, for example, helium.

The calcination is carried out under a condition sufficient to effect the production of tungsten carbide. Such a condition can include a temperature in the range of from about 200 to about 1,500 ° C., preferably about 300 to about 1,200° C., and most preferably 400 to 1,000° C.; for a sufficient period ranging from about 30 minutes to about 20 hours, preferably about 1 hour to 15 hours, and preferably 1 hour to 10 hours; and under a pressure maintaining or accommodating the temperature disclosed above.

The calcined catalyst can be treated with a metal compound to produce a metal-promoted composition, if desired. The treatment or impregnation with a metal compound is well known to one skilled in the art and for the interest of brevity, such treatment or impregnation is omitted herein.

The calcined catalyst, whether it is metal-impregnated or not, can then be treated with a reducing agent. The presently preferred reducing agent is a hydrogen-containing fluid which comprises molecular hydrogen ($H_2$) in the range of from 1 to about 100, preferably about 5 to about 100, and most preferably 10 to 100 volume %. The reduction can be carried out at a temperature, in the range of from about 250° C. to about 800° C. for about 0.1 to about 10 hours preferably about 300° C. to about 700° C. for about 0.5 to about 7 hours, and most preferably 350° C. to 550° C. for 1 to 5 hours. If the calcined zeolite is not first treated with a reducing agent, the composition of the present invention can be treated with a reducing agent as described herein prior to use of the composition of the invention.

According to the third embodiment of the present invention, a process useful for converting a $C_9$+ aromatic compound, naphthalene, or both to a $C_6$ to $C_8$ aromatic hydrocarbon comprises, consists essentially of, or consists of contacting a fluid stream comprising a $C_9$+ aromatic compound, in the presence of a catalyst composition, with a hydrogen-containing fluid under a condition sufficient to effect the conversion of a $C_9$+ aromatic compound to a $C_6$ to $C_8$ aromatic hydrocarbon. The catalyst composition is the same as that disclosed in the first embodiment, and can be produced by the second embodiment, of the invention. The term "fluid" is used herein to denote gas, liquid, vapor, or combination thereof. The term "$C_9$+ aromatic compound" is referred to, unless otherwise indicated, as a substituted aromatic compound containing at least 9 carbon atoms per molecule. Preferably the substituted aromatic compound has the formula of $R_nAr$ wherein each R is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, n is a whole number from 1 to 5, and Ar is a phenyl group. More preferably R is an alkyl radical having 1 to about 10 carbon atoms and the aromatic compound has 9 to about 16 carbon atoms per molecule. Most preferably the aromatic compound contains 9 to 12 carbon atoms per molecule.

Any fluid which contains a $C_9$+ aromatic compound as disclosed above can be used as the feed for the process of this invention. The origin of this fluid feed is not critical. However, the preferred $C_9$+ aromatic compounds are derived from the heavies fraction of a product from a paraffin, in particular gasoline, aromatization reaction. Generally, this heavies fraction contains primarily trimethylbenzenes such as 1,2,3-trimethylbenzene, 1,2,4-trimethylbenzene, and 1,3,5-trimethylbenzene and tetramethylbenzenes such as 1,2,3,4-tetramethylbenzene, 1,2,3,5-tetramethylbenzene and 1,2,4,5-tetramethylbenzene. Additionally, n-propylbenzene, 3-ethyltoluene, 4-ethyltoluene, 3-n-propyltoluene, 4-n-propyltoluene, and 1,3-diethylbenzene can also be present in the fluid. Benzene, toluene, ethylbenzene and xylenes are generally substantially absent from the fluid, i.e., the amount of each of these aromatic hydrocarbons is less than about 0.1 weight %. Thus, there is no significant alkylation of these lower aromatic hydrocarbons by the $C_9$+ aromatic compound, i.e., no significant transalkylation occurs as a side-reaction in the process of this invention. However, in a transalkylation reaction, benzene, toluene, xylenes, ethylbenzene, or combinations of two or more thereof can be present in the fluid feed stream in an amount from about 1 to about 50 weight % of the fluid stream.

Any hydrogen-containing fluid which comprises, consists essentially of, or consists of, molecular hydrogen ($H_2$) can be used in the process of this invention. This hydrogen-containing fluid can therefore contain $H_2$ in the range of from about 1 to about 100, preferably about 5 to about 100, and most preferably 10 to 100 volume %. If the $H_2$ content in the fluid is less than 100%, the remainder of the fluid may be any inert gas such as, for example, $N_2$, He, Ne, Ar, steam, or combinations of any two or more thereof, or any other fluid which does not significantly affect the process or the catalyst composition used therein.

The contacting of a fluid containing a $C_9$+ aromatic compound and a hydrogen-containing fluid in the presence of the catalyst composition can be carried out in any technically suitable manner, in batch, semicontinuous, or continuous process under a condition effective to convert a $C_9$+ aromatic compound to a $C_6$ to $C_8$ aromatic hydrocarbon, and in any suitable reaction vessels or reactors known to one skilled in the art. Generally, a fluid containing a $C_9$+ aromatic compound, preferably being in the vaporized state, and a hydrogen-containing fluid are introduced into a fixed catalyst bed, or a moving catalyst bed, or a fluidized catalyst bed, or combinations of any two or more thereof by any means known to one skilled in the art such as, for example, pressure, meter pump, and other similar means. The condition can include an hourly space velocity (HSV) of the $C_9$+ aromatic compound fluid stream in the range of about 0.01 to about 100, preferably about 0.05 to about 50, and most preferably 0.1 to 30 g feed/g catalyst/hour. The hydrogen-containing fluid hourly space velocity generally is in the range of about 1 to about 10,000, preferably about 5 to about 7,000, and most preferably 10 to 5,000 $ft^3$ $H_2/ft^3$ catalyst/hour. The preferred molar ratio of $H_2$ to the $C_9$+ aromatic compound can be in the range of from about 0.01:1 to about 20:1, preferably about 0.1:1 to about 10:1, and most preferably 1:1 to 8:1. Generally, the pressure can be in the range of from about 30 to about 1000 psig, preferably about 50 to about 750 psig, and most preferably 200 to 600 psig, and the temperature is about 250 to about 1,000° C., preferably about 450 to about 750° C.

The process effluent generally contains a heavies fraction of unconverted $C_9$+ aromatics and other heavy ($C_9$+) aromatic compounds which may have been formed by side-reactions (such as isomerization); a lights fraction of alkanes, mainly methane, ethane, propane, n-butane, isobutane, and minor amounts (about 0.1 to about 5 weight %) of $C_5$ alkanes (isopentane and n-pentane); and a BTX aromatic hydrocarbons fraction (benzene, toluene, ortho-xylene, meta-xylene and para-xylene). Generally, the effluent can be separated into these principal fractions by fractionation distillation which is well known to one skilled in the art. The heavies fraction can be recycled to a hydrodealkylation reactor, the lights fraction can be used as fuel gas or as a feed for other reactions such as, for example, in a thermal cracking process to produce ethylene and propylene, and the BTX fraction can be further separated into individual $C_6$ to $C_8$ aromatic hydrocarbon fractions. Alternatively, the BTX fraction can undergo one or more reactions either before or after separation to individual $C_6$ to $C_8$ hydrocarbons so as to increase the content of the most desired BTX aromatic hydrocarbon. Suitable examples of such subsequent $C_6$ to $C_8$ aromatic hydrocarbon conversions are disproportionation of toluene (to form benzene and xylenes), transalkylation of benzene and xylenes (to form toluene), and isomerization of meta-xylene and/or ortho-xylene to para-xylene.

After the catalyst composition has been deactivated by, for example, coke deposition or feed poisons, to an extent that the feed conversion and/or the selectivity to the most valuable $C_6$ to $C_8$ aromatic product (generally xylenes) have become unsatisfactory, the catalyst composition can be reactivated by any means known to one skilled in the art such as, for example, calcining in air to burn off deposited coke and other carbonaceous materials, such as oligomers or polymers, preferably at a temperature of about 400 to about 650° C., followed by a treatment with a reducing agent such as, for example, with hydrogen gas at a temperature of about 400 to about 600° C. The optimal time periods of the calcining and treatment with a reducing agent depend generally on the types and amounts of deactivating deposits on the catalyst composition and on the calcination and reduction temperatures. These optimal time periods can easily be determined by those possessing ordinary skills in the art and are omitted herein for the interest of brevity.

The following examples are presented to further illustrate this invention and are not to be construed as unduly limiting the scope of the present invention.

EXAMPLE I

This example illustrates the preparation of catalyst compositions of the invention.

First, a tungsten hexachloride solution was prepared. The solution contained 8.6 g of guanidine hydrogen chloride, 58.68 g of ethanol (75 ml), and 12 g of tungsten chloride ($WCl_6$). This solution was employed in the Examples for producing tungsten carbide-promoted zeolites.

An alumina-bound beta zeolite (30/70 by weight) having the topology identified as BEA obtained from UOP Incorporated, Des Plaines, Ill. (obtained as a 1/16 inch extrudate) was used in the preparation of the catalyst compositions of the invention. First, 33.50 grams of the zeolite was added to 100 ml of a 6N HCl in a flask to prepare a suspension. The suspension was then heated at 94° C. for 1 hour to prepare an acid-treated zeolite. Thereafter, the spent acid solution was discarded by decantation. The acid-treated zeolite was then washed with a running tap water for about 30 minutes. The washed, acid-treated zeolite was then air-dried. The air-dried, acid-treated zeolite was then subject to calcining at 525° C. for 6 hours to prepare an acid-leached zeolite. A total of 22.75 g of the acid-leached zeolite was produced.

A portion (6 g) of the acid-leached zeolite was then combined with 5.99 g of the above-described tungsten hexachloride solution under an incipient wetness condition to prepare a tungsten-impregnated zeolite which was subject to drying as described above, and thereafter, to calcining at 750° C. for 2 hours in the presence of a helium flow (200 ml/min). The resulting product (6.20 g) was tungsten carbide-impregnated or -promoted zeolite or the composition of the invention (catalyst A). The tungsten carbide phase could be detected by x-ray powder diffraction analysis.

In a separate run, 10.59 grams of beta zeolite BEA obtained as described above was first air-calcined in a muffle furnace at 525° C. for 2 hours followed by impregnation with 7.62 g of the tungsten hexachloride solution followed by calcination as described above for producing catalyst A. This run produced 11.18 g of tungsten carbide-promoted zeolite (catalyst B).

EXAMPLE II

These examples illustrate compositions prepared from zeolites other than beta zeolite.

An aluminum-bound mordenite zeolite (30/70 by weight) (CVB-20A) (60 g) obtained from PQ (Conshohocken, Pa.) was calcined in a muffle furnace at 538° C. for 6 hours to produce 58.56 g of calcined mordenite which was then treated with an HCl solution (60 g concentrated HCl diluted with 60 g $H_2O$) at 80° C. for two hours followed by washing in a running tap water and drying at 500° C. for 4 hours to produce 48.29 g of acid-leached mordenite. Of this, 9.87 g was impregnated with 6.83 g of the tungsten hexachloride solution described in Example I followed by calcining in a helium flow (200 ml/min) at 750° C. for 2 hours to produce 10.07 g of tungsten carbide-promoted mordenite (catalyst C).

Similarly, 10 g of an aluminum-bound Y-zeolite (30/70 by weight) (Y-84) obtained from UOP was treated with a solution containing 10 g HCl and 10 g H20 at 90° C. for 2 hours to produce an acid-leached Y-zeolite. The acid-leached Y-zeolite was then impregnated with 6.08 g of the tungsten hexachloride solution followed by calcining in a hot helium flow as described above to produce 7.67 g of a tungsten carbide-promoted Y-zeolite (catalyst D).

In a separate run, 10 g of an alumina-bound mazzite zeolite (30/70 by weight) obtained from UOP Incorporated, Des Plaines, Ill., was used to prepare 7.64 g of a tungsten carbide-promoted mazzite zeolite (catalyst E), following the procedure described above for producing catalyst D.

In another separate run, 9.90 g of a tungsten carbide-promoted mordenite (catalyst F) was produced from 10 g of mordenite, following the procedure described above for producing catalyst D.

Also in a separate run, a tungsten carbide-promoted mordenite (catalyst G) was prepared using the same procedure described above for catalyst F except that the starting mordenite (10.58 g) had been previously calcined at 525 ° C. for 2 hours and the tungsten hexachloride solution used was 5.83 g.

EXAMPLE III

This example illustrates the use of the catalyst compositions described in Examples I-II as catalysts in the transalkylation of a $C_9$+ aromatic compound and toluene to BTX.

A stainless-steel reactor tube (2.5 cm×50 cm) was filled with a 20 ml bottom layer of Alundum® alumina (inert, low surface area alumina) 5 ml of one of the catalysts (in 1/16 inch extrudates), and a 20 ml top layer of Alundum® alumina. The catalyst was pretreated with flowing hydrogen gas (flow rate: 260 ml $H_2$ per minute) at a temperature being raised from room temperature to a final temperature of 450° C. at a ramping rate of 10° C. per minute. Then the liquid feed, which contained $C_9$+ aromatic compounds and naphthalene, was introduced at a rate of 40 ml/hour, together with hydrogen gas at a rate of 260 ml $H_2$/minute. The weight hourly space velocity of about 7.8 g feed/g catalyst/hour. The reaction temperature was about 500° C. as shown in Table II and the reaction pressure was 550 psig. The reactor effluent was cooled and separated into a gaseous phase and a liquid phase. Both phases were analyzed by gas chromatographs at intervals of about 1 hour.

The liquid feed in the transalkylation runs was heavy $C_9$+ aromatic compounds obtained in a gasoline aromatization test. Toluene was added to the feed such that toluene was present in the feed at about 50 weight %.

The composition of aromatic compounds, up to 12 carbons per molecule, of the feed used for the transalkylation is shown in Table I. There were some paraffins, isoparaffins, and naphthenes as well as numerous unidentified components in the feed that are not shown in Table I.

TABLE I[a]

| | | |
|---|---|---|
| Aromatics (weight %) | $C_6$ | 0.000 |
| | $C_7$ | 50.248 |
| | $C_8$ | 0.411 |
| | $C_9$ | 11.315 |
| | $C_{10}$ | 12.664 |
| | $C_{11}$ | 9.457 |
| | $C_{12}$ | 3.001 |
| | Total | 87.096 |
| Sulfur (ppmw) | | 658 |

[a]$C_7$ was toluene.

Table II below illustrates the production of BTX from the Table I feed and individual catalyst compositions produced in Examples I-II.

TABLE II

Transalkylation Using Zeolite Supported Tungsten-Carbide Catalysts

| Catalyst | Zeolite[a] | Time (hr) | Temp (° C.) | wt % Conv $C_9$+ | wt % Conv Naph | wt % Xylenes |
|---|---|---|---|---|---|---|
| A | BEA (AL) | 6.62 | 497 | 62.503 | 76.560 | 20.450 |
| B | BEA (AC) | 7.35 | 501 | 58.479 | 66.935 | 15.224 |
| C | MOR (AL) | 7.45 | 494 | 34.338 | 59.696 | 4.988 |
| D | Y (AL) | 6.70 | 494 | 31.658 | 33.605 | 3.507 |
| E | MAZ (AL) | 7.00 | 505 | 32.031 | 54.870 | 3.566 |
| F | MOR (none) | 6.70 | 494 | 31.658 | 33.605 | 3.507 |
| F | MOR (AC) | 6.88 | 505 | 32.031 | 54.870 | 3.566 |

[a]The zeolites were BEA, beta-zeolite; Y, Y-zeolite; MAZ, Mazzite; and MOR, mordenite that were pretreated by AC, air-calcining; AL, acid-leaching; and none, no pretreatment.

The results presented in Table II demonstrate that among the large pore zeolites tested, only beta zeolite (catalysts A and B) showed high conversion of $C_9$+ aromatic compounds and naphthalenes as well as high weight % xylenes.

Table II further demonstrates that beta zeolite pretreated with an acid (catalyst A) significantly increased such conversion and weight % xylenes in the product stream, as compared with the beta zeolite pretreated with heat (air calcination).

Reasonable variations, modifications and adaptations for various usages and conditions can be made within the scope of the disclosure and the appended claims, without departing from the scope of this invention.

That which is claimed is:

1. A process comprising contacting, in the presence of a catalyst composition, a fluid which comprises at least a $C_9$+ aromatic compound, with a hydrogen-containing fluid under a condition sufficient to effect the conversion of a $C_9$+ aromatic compound to a $C_6$ to $C_8$ aromatic hydrocarbon wherein said catalyst composition comprises a beta zeolite having incorporated therein tungsten carbide.

2. A process according to claim 1 wherein the weight ratio of tungsten to beta zeolite is in the range of from about 0.0001:1 to about 0.5:1.

3. A process according to claim 1 wherein the weight ratio of tungsten to beta zeolite is in the range of from 0.01:1 to 0.1:1.

4. A process according to claim 1 wherein said tungsten carbide is impregnated on said beta zeolite.

5. A process according to claim 4 wherein the weight ratio of tungsten to beta zeolite is in the range of from 0.01:1 to 0.1:1.

6. A process according to claim 4 wherein the weight % said tungsten carbide is in the range of from 1 to 20%.

7. A process according to claim 1 wherein the weight % said tungsten carbide is in the range of from 1 to 20%.

8. A process according to claim 1 wherein said catalyst composition is prepared by the steps comprising: (1) contacting a beta zeolite with an acid to produce an acid-leached beta zeolite; (2) contacting said acid-leached beta zeolite with an effective amount of a mixture comprising tungsten-containing compound under a condition sufficient to effect the incorporation of said tungsten-containing compound into said zeolite to produce a tungsten-incorporated zeolite; and (3) calcining said tungsten-incorporated zeolite under a condition sufficient to effect the conversion of said tungsten-containing compound into tungsten carbide wherein said acid is selected from the group consisting of sulfuric acid, hydrochloric acid, nitric acid, phosphoric acid, ammonium sulfate, ammonium chloride, ammonium nitrate, formic acid, acetic acid, trifluoroacetic acid, citric acid, trichloroacetic acid, p-toluenesulfonic acid, methanesulfonic acid, partially neutralized acids wherein one or more protons thereof have been replaced with a metal, and combinations of any two or more thereof;

said tungsten-containing compound is selected from the group consisting of tungsten hexachloride, tungsten tetrachloride, tungsten pentachloride, tungsten, hexabromide, tungsten tetrabromide, tungsten pentabromide, tungsten, hexafluoride, tungsten tetrafluoride, tungsten pentafluoride, tungsten hexacarbonyl, tungsten oxychloride, tungsten, hexasulfide, tungsten tetrasulfide, tungsten pentasulfide, ammonium metatungstate, sodium metatungstate, potassium metatungstate, tungstic acid, and combinations of two or more thereof;

said mixture comprises a carbon-nitrogen compound selected from the group consisting of guanidine, urea, cyanamide, dicyanamide, carbon nitrile, dicyandiamide, cyanoguanidine, and combinations of any two or more thereof; and said mixture further comprises a solvent selected from the group consisting of alcohols, ketones, ethers, esters, amides, and combinations of two or more thereof.

9. A process according to claim 8 wherein said acid is hydrochloric acid and said mixture comprises tungsten hexachloride, guanidine hydrochloride, and ethanol.

10. A process according to claim 9 wherein said beta zeolite is combined with alumina prior to being contacted with said acid.

* * * * *